US00PP26550P3

(12) United States Plant Patent
O'Neill

(10) Patent No.: US PP26,550 P3
(45) Date of Patent: Mar. 29, 2016

(54) ***BOUGAINVILLEA* PLANT NAMED 'VISTA2'**

(50) Latin Name: *Bougainvillea communis*
Varietal Denomination: Vista2

(71) Applicant: Jerome O'Neill, Juana Diaz, PR (US)

(72) Inventor: Jerome O'Neill, Juana Diaz, PR (US)

( * ) Notice: Subject to any disclaimer, the term of this patent is extended or adjusted under 35 U.S.C. 154(b) by 135 days.

(21) Appl. No.: 13/998,814

(22) Filed: Dec. 9, 2013

(65) Prior Publication Data

US 2015/0163982 P1 Jun. 11, 2015

(51) Int. Cl.
*A01H 5/00* (2006.01)

(52) U.S. Cl.
USPC ..... Plt./256

(58) Field of Classification Search
USPC ..... Plt./256
See application file for complete search history.

*Primary Examiner* — Keith Robinson
(74) *Attorney, Agent, or Firm* — Cassandra Bright

(57) ABSTRACT

A new and distinct *Bougainvillea* cultivar named 'Vista2' is disclosed, characterized by orange bracts. Plants are very compact. The new variety is a *Bougainvillea*, typically produced as an ornamental plant.

1 Drawing Sheet

Latin name of the genus and species: *Bougainvillea communis.*

Variety denomination: 'Vista2'.

BACKGROUND OF THE INVENTION

The new cultivar is the product of chance discovery. The new variety originated as naturally occurring whole plant mutation of the unpatented variety *Bougainvillea communis* 'Flame'. The inventor discovered the variety in a commercial planting of the parent variety in Juana Diaz, Puerto Rico in August of 2012.

After identifying the interesting flower color mutation, the inventor observed the single plant mutation for several months. First propagation was performed by vegetative cuttings during October 2012, in Juana Diaz, Puerto Rico. Access to all plants was restricted, as plants were kept in a facility belonging to the inventor and not open to the public.

Through subsequent propagation by vegetative cuttings, multiple generations have been reproduced, which have shown that the unique features of this cultivar are stable and reproduced true to type.

SUMMARY OF THE INVENTION

The cultivar 'Vista2' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Vista2'. These characteristics in combination distinguish 'Vista2' as a new and distinct *Bougainvillea* cultivar:

1. Very compact growth habit
2. Color of mature bract is orange

PARENT COMPARISON

Plants of the new cultivar 'Vista2' are similar to the parent, in most horticultural characteristics. The new variety, however, produces bracts that are orange in color, whereas bracts of the parent variety are an orange-red.

COMMERCIAL COMPARISON

Plants of 'Vista2' are similar in some horticultural characteristics to the variety *Bougainvillea* 'Rijnbo710', U.S. Plant Pat. No. 21,009. The new variety, however, produces smaller foliage, and flowers bracts with orange coloration, whereas 'Rijnbo710' has red-purple bracts. Additionally, inflorescence of 'Vista2' are not as tightly compact as inflorescence of 'Rijnbo710'. Plants of the new variety are more compact than plants 'Rijnbo710'.

Plants of 'Vista2' are similar in most horticultural characteristics to the variety *Bougainvillea* 'Vista1', application Ser. No. 13/986,855. The new variety, however, flowers bracts with orange coloration, whereas 'Vista1' has mainly red bracts.

BRIEF DESCRIPTION OF THE PHOTOGRAPH

The accompanying photograph in FIG. 1 illustrates in full color a typical plant of 'Vista2' grown in a commercial greenhouse in Juana Diaz, Puerto Rico.

This plant is approximately 6 months old, shown planted in a 6 inch container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe a 'Vista2' plant. This plant was grown in a greenhouse in a commercial 6 inch pot, in Juana Diaz, Puerto Rico. The plant described is approximately 6 months old. Temperatures ranged from 15° C. at night and 18° C. to 24° C. during the day. No artificial light, photoperiodic treatments were given to the plants. Measurements and numerical values represent averages of typical plant types.

Botanical classification: *Bougainvillea communis* 'Vista2'.

PROPAGATION

Time to initiate roots: 14-21 days at approximately 25° C.

Root description: Roots are fine, fibrous and well branched.

Time to produce a rooted plant: Approximately 6 to 12 weeks.

Root color: Near Grey-Brown 199D and Greyed-Yellow 161D.

PLANT

Growth habit: This plant is an upright tender perennial, suitable for indoor ornamental use, or outdoor garden use in warm climates.

Pot size of plant described: 6 inch.

Height: 15 cm.

Plant spread: 20 cm.

Main stem color: Grey-Brown 199B.

Main stem texture: Smooth, scaly.

Branching characteristics: Not free branching, moderate branching can be achieved with pinching.

Length of primary lateral branches: 7-11 cm.

Quantity of primary lateral branches: 3 per plant.

Characteristics of primary lateral branches:

- *Diameter*.—Approximately. 0.3 cm.
- *Color*.—Near RHS Grey-Purple 183C.
- *Texture*.—Dull, scaly.

Internode length: 0.9 cm to –2.0 cm.

FOLIAGE

Leaf:

- *Arrangement*.—Alternate, simple.
- *Quantity*.—Approximately 8 per branch on a 6 month old plant.
- *Average length*.—Approximately 3.2 cm.
- *Average width*.—Approximately. 2.3 cm.
- *Shape of blade*.—Elliptical.
- *Apex*.—Acute.
- *Base*.—Acute.
- *Margin*.—Entire.
- *Texture of top surface*.—Smooth.
- *Texture of bottom surface*.—Smooth.
- *Appearance of top surface*.—Glossy.
- *Appearance of bottom surface*.—Matte.
- *Color*.—Young foliage upper side: Near RHS Greyed-Orange 175A. Young foliage under side: Near RHS Greyed-Orange 174A. Mature foliage upper side: Near RHS Green 137A. Mature foliage under side: Near RHS Green 137A.
- *Venation*.—Type: Pinnate. Venation color upper side: RHS Yellow-Green 144B. Venation color under side: RHS Yellow-Green N144B.
- *Petiole*.—Length: 1.1 cm. Diameter: 0.2 cm. Color: Near RHS Yellow-Green N144A. Texture: Smooth.

Other characteristics:

- *Thorns*.—One thorn is above each leaf. Thorn is pointed downwards; Young thorns are soft. Old thorns are very sharp and strong. Average thorn length: 1.5-2.0 cm. Average thorn width at base: 0.2 cm. Thorn curvature: Absent to weak. Thorn coloration: Young thorns near RHS Grey-Brown N199C. Old thorns RHS Grey-Brown N199A.

FLOWER

Normal flowering period: Continuously from early Spring through Fall in Puerto Rico.

Inflorescence:

- *Form*.—Axillary, compact cyme.
- *Width of entire inflorescence*.—10 cm.
- *Height of entire inflorescence*.—7 cm.
- *Quantity of individual flowers in inflorescence*.—Avg. 3 on a 6 month old plant.

Flower longevity on plant: Approximately 10 days.

Quantity of inflorescence per plant: Avg. 4.

Quantity of bract clusters: Medium density. Average range 8 to 12 on a 6 month old plant.

Persistent or self-cleaning: Self-cleaning.

Bud:

- *Shape*.—Oblanceolate with sharp apex.
- *Length*.—0.4 cm.
- *Diameter*.—0.3 cm.
- *Color*.—Near RHS Red 40B.

Individual true flower:

- *Form/type*.—Single, tubular flowers growing from the base of a single bract. The flowers have no petals or sepals. The individual true "flower" is small, and each cluster of three flowers is surrounded by three bracts. Sometimes the cluster consists of more flowers but the number of bracts is nearly always 3.
- *Diameter*.—0.8 cm.
- *Depth*.—0.25 cm.
- *Days lasting on plant*.—Approximately one week.

Petals: No petals.

Bracts:

- *Days lasting on plant*.—Approximately 10, self-cleaning.
- *Type*.—Single.
- *Shape*.—Deltoid.
- *Length*.—3.4 cm.
- *Width*.—2.0 cm.
- *Tip*.—Acute.
- *Base*.—Rounded.
- *Margin*.—Entire.
- *Aspect*.—Undulated.
- *Color*.—Under side of immature bract: RHS Orange 28A. Upper side of immature bract: RHS Orange N25A. Under side of mature bract: RHS Orange N25A. Upper side of mature bract: RHS Orange 28A. Bract vein color on under side: RHS Orange-Red N34A. Bract vein color on upper side: RHS Green 143B.

Sepals: No sepals observed.

Peduncles:

- *Length*.—Average 4.5 cm.
- *Diameter*.—0.2 cm.
- *Angle*.—Approximately 70-90° to the lateral branch.
- *Strength*.—Moderately strong.
- *Texture*.—Smooth.
- *Color*.—Near RHS Greyed-Orange 173A.

Pedicels:

- *Arrangement*.—Individual flowers in whorls of 3, together on pedicels. Each individual flower sessile, implanted in a colorful bract.
- *Length*.—2.2 cm.

*Diameter.*—0.1 cm.
*Angle.*—Average angle of 45 degrees.
*Strength.*—Moderately strong.
*Color.*—Near RHS Greyed-Orange 174A.

Fragrance: None.

REPRODUCTIVE ORGANS

Stamens:
*Number.*—Average 8.

Anthers:
*Length.*—Approximately 0.05 cm.
*Color.*—Near Yellow 7A.
*Pollen.*—Color RHS Yellow-Orange 15A. Quantity: Scant.

Pistil:
*Number.*—1.
*Length.*—0.5 cm.
*Style.*—Length: 0.1 cm. Color: RHS Yellow-Green 145C.
*Stigma.*—Shape: Lineate. Color: Near RHS Yellow Green 146C. Ovary Color: Near RHS Yellow Green 145B.

OTHER CHARACTERISTICS

Seeds and fruits: Seed production not observed.

Disease/pest resistance: Neither resistance nor susceptibility to diseases or pests has been observed in this variety.

Temperature tolerance: Tolerates high temperatures to at least 35 degrees Celsius. Frost is not tolerated. When roots are frozen completely, the plant will not recover.

Drought tolerance: No drought tolerance. Leaves and bracts will drop off the plant immediately under dry conditions.

What is claimed is:

1. A new and distinct cultivar of *Bougainvillea* plant named 'Vista2' as herein illustrated and described.

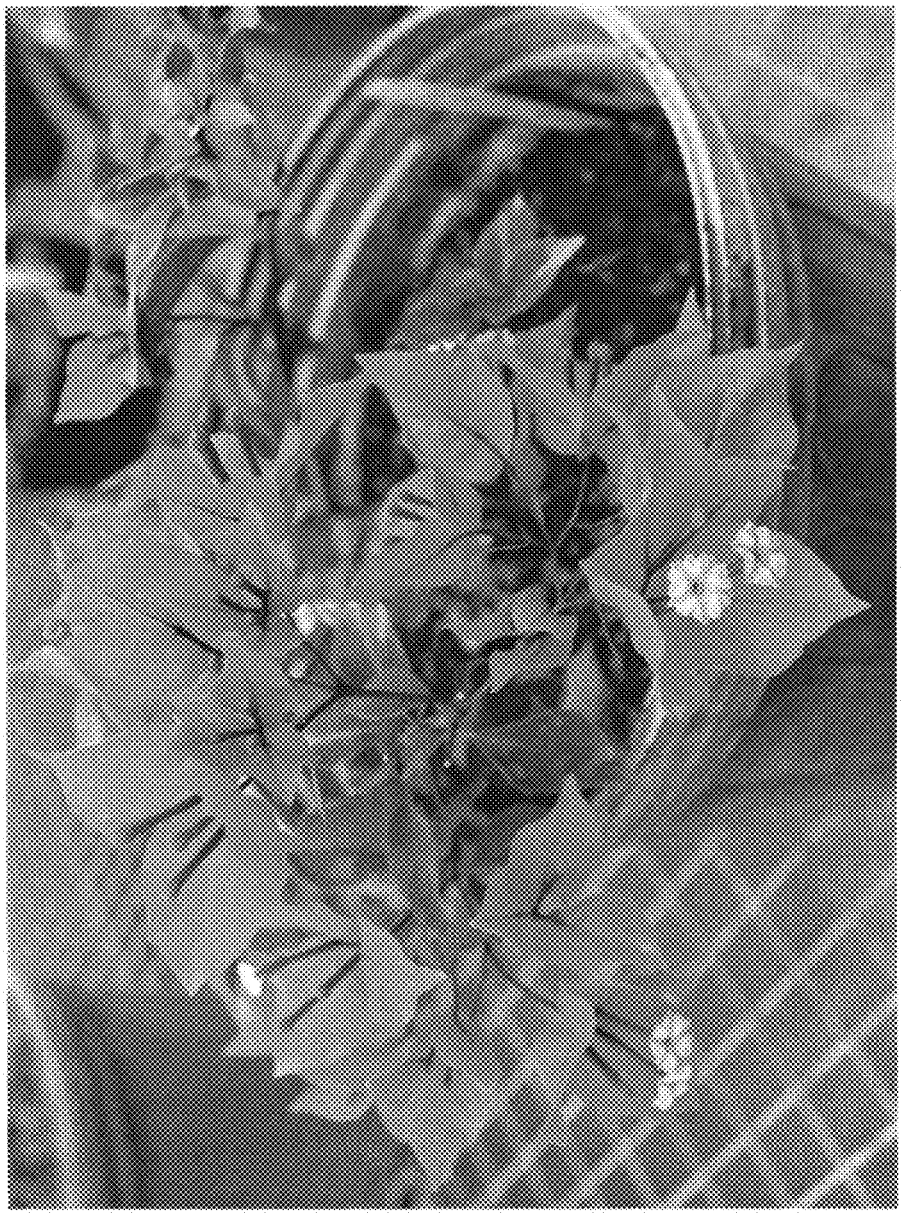

* * * * *